US008003396B2

(12) United States Patent
Hess et al.

(10) Patent No.: US 8,003,396 B2
(45) Date of Patent: Aug. 23, 2011

(54) NT-PROBNP/TROPONIN RATIO FOR ASSESSING MYOCARDIAL DYSFUNCTION

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/748,879

(22) Filed: Mar. 29, 2010

(65) Prior Publication Data

US 2010/0255594 A1    Oct. 7, 2010

Related U.S. Application Data

(63) Continuation of application No. PCT/EP2008/063518, filed on Oct. 9, 2008.

(30) Foreign Application Priority Data

Oct. 10, 2007    (EP) .................................... 07118201

(51) Int. Cl.
*G01N 33/00*    (2006.01)
(52) U.S. Cl. ......................................... 436/86; 422/68.1
(58) Field of Classification Search .......................... None
See application file for complete search history.

(56) References Cited

U.S. PATENT DOCUMENTS 5,744,305 A    4/1998 Fodor et al.

FOREIGN PATENT DOCUMENTS

| EP | 0648228 B1 | 11/1998 |
|---|---|---|
| EP | 1837659 A1 | 9/2007 |
| WO | 02/083913 A1 | 10/2002 |
| WO | 2002/089657 A3 | 11/2002 |
| WO | WO-2006/131529 A1 * | 12/2006 |

OTHER PUBLICATIONS

Mega, J. L. et al. "B-Type Natriuretic Peptide at Presentation and Prognosis in Patients With ST-Segment Elevation Myocardial Infarction," Journal of the American College of Cardiology, 2004, 44, 335-339.*
International Search Report issued Jan. 21, 2009 in PCT Application No. PCT/EP2008/063518.
International Preliminary Report on Patentability issued Apr. 13, 2010 in PCT Application No. PCT/EP2008/063518.
Anderson, Page A. W. et al., Molecular Basis of Human Cardiac Troponin T Isoforms Expressed in the Developing, Adult, and Failing Heart, Circulation Research, 1995, pp. 681-686, vol. 76, No. 4.
Beck-Da-Silva, Luis et al., Brain natriuretic peptide predicts successful cardioversion in patients with atrial fibrillation and maintenance of sinus rhythm, Canadian Journal of Cardiology, Oct. 2004, pp. 1245-1248, vol. 20, No. 12.
Bonow, Robert O., New Insights Into the Cardiac Natriuretic Peptides, Circulation, 1996, pp. 1946-1950, vol. 93.
Fonarow, Gregg C. et al., Combining Natriuretic Peptides and Necrosis Markers in Determining Prognosis in Heart Failure, Reviews in Cardiovascular Medicine, 2003, pp. S20-S28, vol. 4, Supplement No. 4.
Ferrieres, Gaelle et al., Human cardiac troponin I: precise identification of antigenic epitopes and prediction of secondary structure, Clinical Chemistry, 1998, pp. 487-493, vol. 44, No. 3.
Joint European Society of Cardiology/American College of Cardiology Committee, Myocardial Infarction Redefined—A Consensus Document of the Joint European Society of Cardiology/American College of Cardiology Committee for the Redefinition of myocardial Infarction, Journal of the American College of Cardiology, 2000, pp. 959-969, vol. 36, No. 3.
Karl, J. et al., Development of a novel, N-Terminal-proBNP (NT-proBNP) assay with a low detection limit, Scandianavian Journal of Clinical Laboratory Investigation, 1999, pp. 177-181, vol. 59, Supplement 230.
Latini, Roberto et al., Prognostic Value of Very Low Plasma Concentrations of Troponin T in Patients with Stable Chronic Heart Failure, Circulation, 2007, pp. 1242-1249, vol. 116.
Mueller, Thomas et al., Long-term stability of endogenous B-type natriuretic peptide (BNP) and amino terminal proBNP (NT-proBNP) in frozen plasma samples, Clinical Chem Lab Med, 2004, pp. 942-944, vol. 42.
Nolan, James P. and Sklar, Larry A., Suspension array techonology: evolution of the flat-array paradigm, Trends in Biotechnology, Jan. 2002, pp. 9-12, vol. 20, No. 1.
Smith, M. W. et al., Delayed metabolism of human brain natriuretic peptide reflects resistance to neutral endopeptidase, Journal of endocrinology, 2000, pp. 239-246, vol. 167.
Taniguchi, Ryoji et al., Combined Measurements of Cardiac Troponin T and N-Terminal Pro-Brain Natriuretic Peptide in Patients With Heart Failure, Circulation Journal, Dec. 2004, pp. 1160-1164, vol. 68.

(Continued)

*Primary Examiner* — Yelena G. Gakh
*Assistant Examiner* — Michelle Adams
(74) *Attorney, Agent, or Firm* — Roche Diagnostics Operations, Inc.

(57) ABSTRACT

The present invention relates to a method of diagnosing if a subject which has suffered from an acute myocardial infarction is also suffering from a pre-existing myocardial dysfunction, the method comprising a) determining the amount of a natriuretic peptide in a sample of the subject; b) determining the amount of a cardiac troponin in a sample of the subject; c) calculating the ratio (natriuretic peptide/cardiac troponin); and d) diagnosing if the elevated natriuretic peptide level is related to a preexisting myocardial dysfunction or if the elevated level is caused by the acute myocardial infarction, based on the ratio calculated in step c). The method allows determining whether the individual has suffered from a myocardial dysfunction, in particular heart failure, before the myocardial infarction has occurred.

11 Claims, No Drawings

OTHER PUBLICATIONS

Taniguchi, Ryoji et al., Measurments of baseline and follow-up concentrations of cardiac troponin-T and brain natriuretic peptide in patients with heart failure from various etiologies, Heart Vessels, 2006, pp. 344-349, vol. 21.

Tsuchida, Keizo and Tanabe, Kazuhiko, Influence of Paroxysmal Atrial Fibrillation Attack on Brain Natriuretic Peptide Secretion, Journal of Cardiology, Jul. 2004, pp. 1-11, vol. 44, No. 1.

Wu, Alan H. B. et al., Analytical and Clinical Evaluation of the Bayer ADVIA Centaur automated B-Type Natriuretic Peptide Assay in Patients with Heart Failure: A Multisite Study, clinical Chemistry, 2004, pp. 867-873, vol. 50, No. 5.

Yeo, Kiang-Teck J. et al., Multicenter evaluation of the Roche NT-proBNP assay and comparison to the Biosite Triage BNP assay, Clinica Chemica Acta, 2003, pp. 107-115, vol. 338.

* cited by examiner

NT-PROBNP/TROPONIN RATIO FOR ASSESSING MYOCARDIAL DYSFUNCTION

RELATED APPLICATIONS

This application is a continuation of PCT/EP2008/063518 filed Oct. 9, 2008 and claims priority to EP 07118201.8 filed Oct. 10, 2007.

FIELD OF THE INVENTION

The present invention is concerned with methods and devices for medical diagnosis. Specifically, it relates to a method of discriminating if an elevated amount of a natriuretic peptide in a sample of a subject which has suffered from an acute myocardial infarction has been caused by the acute event of myocardial infarction, or if the elevated amount is related to a myocardial dysfunction which existed before the myocardial infarction occurred, or is related to a combination of both. Said method comprises determining the amounts of a natriuretic peptide and of a cardiac troponin in a sample of said subject and diagnosing, from the ratio of the natriuretic peptide to the cardiac troponin, if the patient is suffering from a cardiovascular disorder. Moreover, the present invention relates to a diagnostic device and a kit for carrying out the aforementioned method.

BACKGROUND

An aim of modern medicine is to provide personalized or individualized treatment regimens. Those are treatment regimens which take into account a patient's individual needs or risks. Personalized or individual treatment regimens shall be even taken into account for emergency measures where it is required to decide on potential treatment regimens within short periods of time. Heart diseases are the leading cause of morbidity and mortality in the Western hemisphere. The diseases can remain asymptomatic for long periods of time. However, they may have severe consequences once an acute cardiovascular event, such as myocardial infarction, as a cause of the cardiovascular disease occurs.

Heart failure is a condition that can result from any structural or functional cardiac disorder that impairs the ability of the heart to fill with or pump a sufficient amount of blood throughout the body. Even with the best therapy, heart failure is associated with an annual mortality of about 10%. Heart failure is a chronic disease; it can, inter alia, occur either following an acute cardiovascular event (like myocardial infarction), or it can occur, e.g., as a consequence of inflammatory or degenerative changes in myocardial tissue. Heart failure patients are classified according to the NYHA system in classes I, II, III and IV. A patient having heart failure will not be able to fully restore his health without receiving a therapeutic treatment.

Myocardial dysfunction is a general term, describing several pathological states of the heart muscle (myocard). A myocardial dysfunction may be a temporary pathological state (caused by, e.g., ischemia, toxic substances, and alcohol), contrary to heart failure. Myocardial dysfunction may disappear after removing the underlying cause. A symptomless myocardial dysfunction may, however, also develop into heart failure (which has to be treated in a therapy). A myocardial dysfunction may, however, also be a heart failure, a chronic heart failure, even a severe chronic heart failure.

Myocardial dysfunction and heart failure often remain undiagnosed, particularly when the condition is considered "mild." The conventional diagnostic techniques for heart failure are based on the well known vascular volume stress marker NT-proBNP, a natriuretic peptide. However, the diagnosis of heart failure under some medical circumstances based on NT-proBNP appears to be incorrect for a significant number of patients but not all (e.g., Beck 2004, Canadian Journal of Cardiology 20: 1245-1248; Tsuchida 2004, Journal of Cardiology, 44:1-11). However, especially patients which suffer from heart failure would urgently need a supportive therapy of the heart failure. On the other hand, as a consequence of an incorrect diagnosis of heart failure, many patients will receive a treatment regimen which is insufficient or which may have even adverse side effects.

Patients having heart failure may also develop an acute cardiac disorder, in general an acute coronary syndrome. ACS covers the states of unstable angina pectoris UAP and acute myocardial infarction MI.

MI is classified as belonging to coronary heart diseases CHD and is preceded by other events also classified as belonging to CHD, like unstable angina pectoris UAP. Symptomatic for UAP is chest pain which is relieved by sublingual administration of nitroglycerine. UAP is caused by a partial occlusion of the coronary vessels leading to hypoxemia and myocardial ischemia. In case the occlusion is too severe or total, a myocardial necrosis (which is the pathological state underlying myocardial infarction) results. MI may occur without obvious symptoms, i.e., the subject does not show any discomfort, and the MI is not preceded by stable or unstable angina pectoris.

UAP, however, is a symptomatic event preceding MI. A CHD in a subject may also occur symptomless, i.e., the subject may not feel uncomfortable and exhibit any signs of CHD like shortness of breath, chest pain or others known to the person skilled in the art. The subject, however, may be pathological and suffer from a malfunction of his coronary vessels which may result in a MI and/or congestive heart failure CHF, meaning the heart does not have the capacity to perform as required in order to ensure the necessary provision of blood to the subject's body. This may result in severe complications, one example of which is cardiac death.

Patients suffering from symptoms of an acute cardiovascular event (e.g., myocardial infarction) such as chest pain are currently subjected to a cardiac troponin based diagnosis, generally troponin T or troponin I. To this end, troponin T/I levels of the patients are determined. If the amount of troponin T in the blood is elevated, i.e., above 0.1 ng/ml, an acute cardiovascular event is assumed and the patent is treated accordingly.

However, by exclusively measuring natriuretic peptides, the information obtained does not allow to assess if a myocardial dysfunction already existed prior to the acute myocardial infarction.

An acute myocardial infarction is caused by an occlusion of a heart coronary vessel, resulting in the death of a region of various size of the heart muscle tissue. The death of the myocard causes an elevation of troponin T (a heart-specific molecule) or troponin I, which can be detected in serum/plasma. Furthermore, the death of the myocard is connected with a loss of the pump function of the heart, resulting in an elevated level of natriuretic peptides.

The level of troponin T- and also troponin I- and the natriuretic peptides, in particular NT-proBNP, starts to raise about 4-6 hours after a myocardial infarction. Patients consulting their physician after that time, have an elevated level of the peptides.

With respect to the value of the natriuretic peptides, in particular NT-proBNP, it cannot be assessed if a) the elevated level of the peptide is a consequence of the acute MI, or if
b) the elevated NT-proBNP value already existed prior to the MI, or if
c) the value is caused by both the degeneration of the cardial function by the MI and the pre-existing myocardial dysfunction. It would be desirable to have means and methods permitting to differentiate between the topics laid out beforehand.

The technical problem underlying the present invention can be seen as the provision of means and methods for complying with the aforementioned needs. The technical problem is solved by the embodiments characterized in the claims and herein below.

SUMMARY OF THE INVENTION

Accordingly, the present invention relates to a method of diagnosing if a subject which has suffered from an acute myocardial infarction is also suffering from a pre-existing myocardial dysfunction, said method comprising
a) determining the amount of a natriuretic peptide in a sample of said subject;
b) determining the amount of a cardiac troponin in a sample of said subject;
c) calculating the ratio (natriuretic peptide/cardiac troponin);
d) diagnosing if the elevated natriuretic peptide level is related to a preexisting myocardial dysfunction, or if the elevated level is caused by the acute myocardial infarction, based of the ratio calculated in step c).

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and subclassification of a subject. The method may be carried out manually or assisted by automation. Preferably, step (a) and/or (b) and/or (c) and/or (d) may in total or in part be assisted by automation, e.g., by a suitable robotic and sensory equipment for the determination in steps (a) and/or (b) or a computer-implemented comparison in step (c).

In a preferred embodiment of the present invention, the levels of the natriuretic peptide are measured at a timepoint which lies 1 to 3 days (24 to 72 h) after the acute event has occurred, preferably 36 to 60 h, most preferably about 48 h.

DETAILED DESCRIPTION OF THE INVENTION

The term "diagnosing" as used herein means assessing as to whether a subject having an elevated level of a natriuretic peptide and/or of a cardiac troponin suffers from a pre-existing (i.e., prior to the occurrence of the ACS) myocardial dysfunction, in particular heart failure, or not. As will be understood by those skilled in the art, such an assessment is usually not intended to be correct for all (i.e., 100%) of the subjects to be identified. The term, however, requires that a statistically significant portion of subjects can be identified (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

Diagnosing according to the present invention includes monitoring, confirmation, subclassification and prediction of the relevant disease, symptoms or risks therefor. Monitoring relates to keeping track of an already diagnosed disease. Confirmation relates to the strengthening or substantiating a diagnosis already performed using other indicators or markers. Subclassification relates to further defining a diagnosis according to different subclasses of the diagnosed disease, e.g., defining according to mild and severe forms of the disease.

The term "subject" as used herein relates to animals, preferably mammals, and, more preferably, humans. Preferably, the subject referred to in accordance with the aforementioned method suffers from a myocardial dysfunction, in particular heart failure, and/or myocardial infarction or exhibits the symptoms or clinical parameters, such as an increased NT-proBNP level or an increased troponin T level accompanied therewith, i.e., being at least suspect to suffer from a myocardial dysfunction, in particular heart failure, and/or myocardial infarction.

Therefore, it is not possible to diagnose, from the cardiac troponin level alone, if a subject with an elevated troponin level is also suffering from a myocardial dysfunction, in particular heart failure. In a similar manner, it is not possible to diagnose, from the natriuretic peptide level alone, if a subject with an elevated natriuretic peptide level is also suffering from a myocardial infarction, possibly in connection with a myocardial dysfunction, in particular heart failure.

In order to establish a diagnosis as laid out beforehand, the present invention teaches to measure the level of a natriuretic peptide, further to a cardiac troponin. From the ratio natriuretic peptide/cardiac troponin which is calculated from the values obtained, it is clear whether the subject is suffering only from an acute myocardial infarction, or whether the subject is also suffering from a myocardial dysfunction (which leads to wall stress and, in consequence, to an elevated level of the natriuretic peptide) which has caused the myocardial infarction. The diagnosis obtained in accordance with the teachings of the present invention will allow to target and to control the therapy following the myocardial infarction with greater precision.

According to the present invention, a low ratio (natriuretic peptide/cardiac troponin) is indicative that a myocardial dysfunction was non existent or existed only to a minor extent before MI occurred. A high ratio (natriuretic peptide/cardiac troponin) is indicative for a preexisting (i.e., prior to the MI) myocardial dysfunction. The person skilled in the art is aware that the values indicating a myocardial dysfunction or not may vary, according to the natriuretic peptide the level of which is determined.

Individuals having only a minor myocardial dysfunction prior to MI, or having no myocardial dysfunction at all, redevelop myocardial functionality to at least a high extent after several weeks or months, e.g., 3 months. In contrast, individuals having only a preexisting considerable myocardial dysfunction (prior to MI) hardly redevelop myocardial functionality after several weeks or months. In these cases, a therapy can be initiated immediately after MI has occurred and the ratio (natriuretic peptide/cardiac troponin) is indicative of a preexisting myocardial dysfunction.

The following values are values which have been established for NT-proBNP. Here, preferably, a ratio (natriuretic peptide/cardiac troponin) of >10 (higher than or equal to 10) is indicative for a myocardial dysfunction. A ratio of >5 (higher than or equal to 5) indicates a high probability for the occurrence of a myocardial dysfunction. A ratio of >3 (higher than or equal to 3) indicates a very high probability for the occurrence of a myocardial dysfunction. A ratio of >1 (higher than or equal to 1) indicates a still higher probability for the occurrence of a myocardial dysfunction A ratio (natriuretic peptide/cardiac troponin) of <1 (below 1) indicates that the cardiac troponin value is not or very probably not associated with a myocardial dysfunction. These values may apply for the other natriuretic peptides as well. They may also be different. In the knowledge of the present invention, however, the person skilled in the art knows to adapt the values given above to the other natriuretic peptides, by applying values published in the prior art, or in a routine measurement. replacing NT-proBNP for another natriuretic peptide.

The following values are values which have been established for NT-proBNP independently of troponin T.

Here, preferably, a troponin T level of >3000 pg/ml indicates a strong MI. A value of >1000 to 3000 pg/ml indicates a medium MI. A value of >100 to 1000 pg/ml indicates a small MI. A value of <100 (below 100) indicates that no MI has occurred.

The following values are values which have been established for troponin T independently of NT-proBNP.

Here, preferably, a NT-proBNP level of >2000 pg/ml indicates a strong myocardial dysfunction. A value of >800 to 2000 pg/ml indicates a medium myocardial dysfunction. A value of >300 to 800 pg/ml indicates a small myocardial dysfunction. A value of <125 (below 125) is a normal range, not indicating myocardial dysfunction. These data may vary, depending on age and/or kidney malfunction.

The method according to the present invention comprises determining the amount of cardiac troponin in a sample of said subject, and determining the amount of a natriuretic peptide in a sample of the subject. These steps may be carried out simultaneously, or prior or subsequently.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493.

Preferably, cardiac troponin refers to troponin T and/or troponin I.

Accordingly, both troponins may be determined in the method of the present invention together, i.e., simultaneously or sequentially, or individually, i.e., without determining the other isoform at all.

Amino acid sequences for human troponin T and human troponin I are disclosed in Anderson, loc cit and Ferrieres 1998, Clinical Chemistry, 44: 487-493. The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present invention comprise ANP-type and BNP-type peptides and variants thereof (see, e.g., Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NT-proBNP is 120 min longer than that of BNP, which is 20 min (Smith 2000, J. Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. More preferred natriuretic peptides according to the present invention are BNP and NT-proBNP or variants thereof. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e., epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

As discussed above already, a preferred reference amount serving as a threshold may be derived from the ULN. The ULN for a given population of subjects can be determined as specified elsewhere in this description. A preferred threshold (i.e., reference amount) for a natriuretic peptide and, in particular for NT-proBNP, is at least one times, more preferably two to four times the ULN. Preferably, the ULN for NT-proBNP referred to in this context is 125 pg/ml. ULNs for the other natriuretic peptides are known in the art and are, preferably, 40 pg/ml for ANP, 50 pg/ml for BNP and 800 pg/ml for NT-proANP. An amount of a natriuretic peptide larger than the reference amount is, more preferably, additionally indicative for a subject suffering from heart failure.

The present invention in relates to cardiac disorders, preferably from the group myocardial dysfunction and heart failure.

The term "myocardial dysfunction" as used herein is a general term and relates to several pathological states of the myocard. A myocardial dysfunction may be a temporary pathological state (caused by, e.g., ischemia, toxic substances, and alcohol). Myocardial dysfunction may disappear after removing the underlying cause. In the context of the present invention, the myocardial dysfunction can be a symptomless myocardial dysfunction. A myocardial dysfunction, in particular a symptomless myocardial dysfunction, may also develop into heart failure. A myocardial dysfunction may also be a severe chronic heart failure. In general, a myocardial dysfunction is an impaired systolic and/or diastolic function of the heart, and a myocardial dysfunction may occur with or without heart failure. Any heart failure mentioned beforehand may be symptomless.

The term "heart failure" as used herein relates to an impaired systolic and/or diastolic function of the heart. Preferably, heart failure referred to herein is also chronic heart failure. Heart failure can be classified into a functional classification system according to the New York Heart Association (NYHA). Patients of NYHA Class I have no obvious symptoms of cardiovascular disease but already have objective evidence of functional impairment. Physical activity is not limited, and ordinary physical activity does not cause undue fatigue, palpitation, or dyspnea (shortness of breath). Patients of NYHA class II have slight limitation of physical activity. They are comfortable at rest, but ordinary physical activity results in fatigue, palpitation, or dyspnea. Patients of NYHA class III show a marked limitation of physical activity. They are comfortable at rest, but less than ordinary activity causes fatigue, palpitation, or dyspnea. Patients of NYHA class IV are unable to carry out any physical activity without discomfort. They show symptoms of cardiac insufficiency at rest. Heart failure, i.e., an impaired systolic and/or diastolic function of the heart, can be determined also by, for example, echocardiography, angiography, szintigraphy, or magnetic resonance imaging. This functional impairment can be accompanied by symptoms of heart failure as outlined above (NYHA class II-IV), although some patients may present without significant symptoms (NYHA I). Moreover, heart failure is also apparent by a reduced left ventricular ejection fraction (LVEF). More preferably, heart failure as used herein is accompanied by a left ventricular ejection fraction (LVEF) of less than 60%, of 40% to 60% or of less than 40%.

The term "acute cardiovascular event" refers to all events which suddenly appear, i.e., without previous clinical signs or symptoms, and which severely affect the diastolic or systolic blood flow rate. Histopathologically, the acute cardiovascular event referred to herein shall be accompanied by a sudden ischemia of heart muscle cells accompanied by severe necrosis of said cells. Preferably, the subject suffering from an acute cardiovascular event will also suffer from typical symptoms such as chest, epigastric, arm, wrist or jaw discomfort or pain whereby, in particular, the chest pain may radiate to the arm, back or shoulder. Further symptoms of an acute cardiovascular event may be unexplained nausea or vomiting, persistent shortness of breath, weakness, dizziness, lightheadedness or syncope as well as any combinations thereof. Preferably, the acute cardiovascular event referred to herein is an acute coronary syndrome (ACS), i.e., either an unstable angina pectoris (UAP) or myocardial infarction (MI). Most preferably, the acute cardiovascular event is MI including ST-elevated MI and non-ST-elevated MI. Moreover, the cardiovascular event also encompasses stroke. The occurring of an MI can be followed by a left ventricular dysfunction (LVD). Finally, LVD patients undergo congestive heart failure (CHF) with a considerable mortality rate. Further details on the definitions, symptoms and clinical signs such as electrocardiographic signs, are found in Joint European Society of Cardiology/American Society of Cardiology, 2000, J American College of Cardiology, Vol. 36, No. 3: 959-969.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

Determining the amount of the peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e., a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g., reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on ELECSYS analyzers, Roche Diagnostics GmbH), CBA (an enzymatic Cobalt Binding Assay, available for example on Roche-Hitachi analyzers), and latex agglutination assays (available for example on Roche-Hitachi analyzers).

Preferably, determining the amount of a peptide or polypeptide comprises the steps of (a) contacting a cell capable of eliciting a cellular response the intensity of which is indicative of the amount of the peptide or polypeptide with the peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus hemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels. Enzymatically active labels include, e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the polypeptide or peptide as well as any value or parameter which correlates thereto or can be derived therefrom. Such values or parameters comprise intensity signal values from all specific physical or chemical properties obtained from the peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

Based on the method of the present invention, myocardial dysfunction, in particular heart failure existing prior to an ACS, in particular a MI (and still existing after the acute event) can be diagnosed and treated more efficiently. The method of the present invention, advantageously, allows for a reliable, fast and less cost-intensive diagnosis and can be implemented even in portable assays, such as test stripes. Therefore, the method is particularly well suited for diagnosing emergency patients. Thanks to the findings of the present invention, a suitable therapy for a subject can be timely and reliably selected, e.g., a therapy for heart failure. Severe side effects caused by the late and/or wrong treatment of patients can be avoided.

The present invention, furthermore, relates to a device of diagnosing if a subject which has suffered from an acute myocardial infarction is also suffering from a pre-existing myocardial dysfunction, said device comprising
 a) means for determining the amount of a natriuretic peptide in a sample of said subject;
 b) means for determining the amount of a cardiac troponin in a sample of said subject;
 c) optionally means for calculating the ratio (natriuretic peptide/cardiac troponin);
 d) optionally means for diagnosing if the subject is suffering from a myocardial dysfunction, preferably heart failure, based of the ratio calculated in step c).

The term "device" as used herein relates to a system of means comprising at least the aforementioned means operatively linked to each other as to allow the diagnosis. Preferred means for determining the amount of a cardiac troponin and means for determining the amount of a natriuretic peptide, and means for calculating and diagnosing if the subject is suffering from a cardiovascular disorder are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test stripes are used for determining the amount of the peptides or polypeptides, the means for comparison may comprise control stripes or tables allocating the determined amount to a reference amount. The test stripes are, preferably, coupled to a ligand which specifically binds to the peptides or polypeptides referred to herein. The strip or device, preferably, comprises means for detection of the binding of said peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the clinician. Preferably, the output of the device is, however, processed, i.e., evaluated, raw data the interpretation of which does not require a clinician. Further preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Finally, the present invention relates to a kit of diagnosing if a subject which has suffered from an acute myocardial infarction is also suffering from a pre-existing myocardial dysfunction, said kit comprising instructions for carrying out the method and
- a) means for determining the amount of a natriuretic peptide in a sample of said subject;
- b) means for determining the amount of a cardiac troponin in a sample of said subject;
- c) optionally means for calculating the ratio (natriuretic peptide/cardiac troponin);
- d) optionally means for diagnosing if the subject is suffering from a myocardial dysfunction, preferably heart failure, based of the ratio calculated in step c).

The term "kit" as used herein refers to a collection of the aforementioned means, preferably, provided in separately or within a single container. The container, also preferably, comprises instructions for carrying out the method of the present invention. Accordingly, a kit adopted for carrying out the method of the present invention comprises all components required for practicing said method in a ready-to-use manner, e.g., in a premixed form with adjusted concentrations of the components used for determination and/or comparison.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Specific Embodiments

Example 1

In a cohort of 166 patients showing acute MI, the levels of NT-proBNP, troponin T, C-reactive protein (CRP), growth differentiation factor 15 (GDF 15), and osteopontin were measured. Three months later, the levels of the same peptides were again determined. Patients having a low NT-proBNP/troponin T ratio had a weak or no pre-existing myocardial dysfunction, and a good restitution of the myocard functionality after three months. In contrast to this, patients having a high NT-proBNP/troponin T ratio showed a bad restitution of the myocard function after three months, and a pre-existing myocardial dysfunction.

NT-proBNP levels were determined with an immunoassay on an ELECSYS 2010 with a detection limit of 20 pg/ml.

The results of the study are shown in the following table:

| N = 166 | 41<br>1. quartile | 41<br>2. quartile | 42<br>3. quartile | 42<br>4. quartile |
|---|---|---|---|---|
| | NT-proBNP/hsTnT-Ratio Timepoint 0 | | | |
| Ratio, median (range) | 0.34<br>(0.10-0.56) | 0.86<br>(0.56-1.27) | 2.46<br>(1.32-3.93) | 10.35<br>(4.10-285.02) |
| NT-proBNP [pg/ml], median | 624.10 | 827.2 | 1216.5 | 3369 |
| Hs (high sensitivity) troponin T [pg/ml], median | 1904.5 | 980.4 | 515.45 | 238.25 |
| | NT-proBNP/hsTnT-Ratio Timepoint 3 month | | | |
| NT-proBNP [pg/ml], median | 273.6 | 481.20 | 759.35 | 1245 |
| Hs troponin T [pg/ml], median | 9.80 | 12.8 | 16.10 | 23.85 |

What is claimed is:

1. A method of determining whether a subject who has suffered an acute myocardial infarction had a pre-existing myocardial dysfunction prior to said acute myocardial infarction, said method comprising
    determining an amount of a natriuretic peptide in a sample from said subject,
    determining an amount of a cardiac troponin in a sample from said subject,
    calculating a ratio of natriuretic peptide to cardiac troponin from the amounts determined, and
    determining whether the subject had the pre-existing myocardial dysfunction prior to said acute myocardial infarction based on the ratio calculated.

2. The method of claim 1 wherein a mass ratio of $\geq 10:1$ of natriuretic peptide to cardiac troponin is indicative of the pre-existing myocardial dysfunction.

3. The method of claim 1 wherein a mass ratio of ≧5:1 of natriuretic peptide to cardiac troponin is indicative of the pre-existing myocardial dysfunction.

4. The method of claim 1 wherein the amount of the natriuretic peptide is measured 1 to 3 days after the acute myocardial infarction has occurred.

5. The method of claim 1 wherein the amount of the natriuretic peptide is measured 36 to 60 hours after the acute myocardial infarction has occurred.

6. The method of claim 1 wherein the myocardial dysfunction is heart failure.

7. The method of claim 6 wherein the heart failure is asymptomatic.

8. The method of claim 1 wherein the natriuretic peptide is selected from the group consisting of brain natriuretic peptide (BNP), N-terminal pro-brain natriuretic peptide (NT-proBNP), atrial natriuretic peptide (ANP), and N-terminal pro-atrial natriuretic peptide (NT-proANP)

9. The method of claim 8 wherein the natriuretic peptide is NT-proBNP.

10. The method of claim 1 wherein a mass ratio of <1:1 natriuretic peptide to cardiac troponin indicates the subject did not have the pre-existing myocardial dysfunction.

11. A kit for determining whether a subject who has suffered an acute myocardial infarction had a pre-existing myocardial dysfunction prior to said acute myocardial infarction, said kit comprising a means for determining an amount of a natriuretic peptide in a sample from said subject, a means for determining an amount of a cardiac troponin in a sample from said subject, a means for calculating a ratio of natriuretic peptide to cardiac troponin from the amounts determined, a means for determining whether the subject had the pre-existing myocardial dysfunction prior to said acute myocardial infarction based on the ratio calculated, and instructions for carrying out the method of claim 1.

* * * * *